(12) United States Patent
Fox et al.

(10) Patent No.: US 8,828,031 B2
(45) Date of Patent: Sep. 9, 2014

(54) APPARATUS FOR FORMING AN ANASTOMOSIS

(75) Inventors: William D. Fox, New Richmond, OH (US); Robert M. Trusty, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1017 days.

(21) Appl. No.: 12/352,451

(22) Filed: Jan. 12, 2009

(65) Prior Publication Data

US 2010/0179510 A1    Jul. 15, 2010

(51) Int. Cl.
| | |
|---|---|
| *A61B 17/08* | (2006.01) |
| *A61B 17/11* | (2006.01) |
| *A61B 17/34* | (2006.01) |
| *A61B 17/22* | (2006.01) |
| *A61B 17/00* | (2006.01) |
| *A61B 17/3209* | (2006.01) |
| *A61B 17/29* | (2006.01) |

(52) U.S. Cl.
CPC .............. *A61B 17/1114* (2013.01); *A61B 17/11* (2013.01); *A61B 2017/22038* (2013.01); *A61B 17/3478* (2013.01); *A61B 2017/1139* (2013.01); *A61B 2017/003* (2013.01); *A61B 2017/00557* (2013.01); *A61B 2017/32096* (2013.01); *A61B 2017/2945* (2013.01); *A61B 2017/00876* (2013.01)
USPC ........................................................ 606/153

(58) Field of Classification Search
USPC ............... 606/151, 153–156, 213; 600/12
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |

(Continued)

FOREIGN PATENT DOCUMENTS

| | | |
|---|---|---|
| AU | 666310 B2 | 2/1996 |
| DE | 3008120 A1 | 9/1980 |

(Continued)

OTHER PUBLICATIONS

Michael S. Kavic, M.D., "Natural Orifice Translumenal Endoscopic Surgery: "NOTES"", JSLS, vol. 10, pp. 133-134 (2006).

(Continued)

*Primary Examiner* — Gregory Anderson

(57) ABSTRACT

A surgical instrument, for forming an anastomosis between first and second lumens in a patient, includes a first catheter, a second catheter, a hollow needle, a guide wire, an inflatable member, and a hollow sleeve. The first catheter includes at least one first opening, which may be configured to slidably receive the hollow needle and the guide wire, which may be disposed within the hollow portion of the needle, and at least one second opening. The hollow needle includes a rotary needle. The inflatable member is mounted near the distal end of the first catheter and is in fluid communication with the second opening. The magnet is polarized such that magnetic attraction occurs perpendicular to an axis of the cylindrical body. The hollow sleeve is configured to retain at least a portion of the inflatable member, the guide wire, the hollow needle, and the magnet.

15 Claims, 12 Drawing Sheets

(56) References Cited

U.S. PATENT DOCUMENTS

| | | |
|---|---|---|
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |
| 3,470,876 A | 10/1969 | Barchilon |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A | 12/1990 | Gouda |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,320,636 A | 6/1994 | Slater |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |

(56) References Cited

U.S. PATENT DOCUMENTS

| | | | |
|---|---|---|---|
| 5,401,248 | A | 3/1995 | Bencini |
| 5,403,328 | A | 4/1995 | Shallman |
| 5,403,342 | A | 4/1995 | Tovey et al. |
| 5,403,348 | A | 4/1995 | Bonutti |
| 5,405,073 | A | 4/1995 | Porter |
| 5,405,359 | A | 4/1995 | Pierce |
| 5,409,478 | A | 4/1995 | Gerry et al. |
| 5,417,699 | A | 5/1995 | Klein et al. |
| 5,423,821 | A | 6/1995 | Pasque |
| 5,433,721 | A | 7/1995 | Hooven et al. |
| 5,439,471 | A | 8/1995 | Kerr |
| 5,439,478 | A | 8/1995 | Palmer |
| 5,441,059 | A | 8/1995 | Dannan |
| 5,441,499 | A | 8/1995 | Fritzsch |
| 5,449,021 | A | 9/1995 | Chikama |
| 5,456,667 | A | 10/1995 | Ham et al. |
| 5,456,684 | A | 10/1995 | Schmidt et al. |
| 5,458,131 | A | 10/1995 | Wilk |
| 5,458,583 | A | 10/1995 | McNeely et al. |
| 5,460,168 | A | 10/1995 | Masubuchi et al. |
| 5,460,629 | A | 10/1995 | Shlain et al. |
| 5,462,561 | A | 10/1995 | Voda |
| 5,465,731 | A | 11/1995 | Bell et al. |
| 5,467,763 | A | 11/1995 | McMahon et al. |
| 5,468,250 | A | 11/1995 | Paraschac et al. |
| 5,470,308 | A | 11/1995 | Edwards et al. |
| 5,470,320 | A | 11/1995 | Tiefenbrun et al. |
| 5,478,347 | A | 12/1995 | Aranyi |
| 5,480,404 | A | 1/1996 | Kammerer et al. |
| 5,482,054 | A | 1/1996 | Slater et al. |
| 5,484,451 | A | 1/1996 | Akopov et al. |
| 5,489,256 | A | 2/1996 | Adair |
| 5,496,347 | A | 3/1996 | Hashiguchi et al. |
| 5,499,990 | A | 3/1996 | Schülken et al. |
| 5,499,992 | A | 3/1996 | Meade et al. |
| 5,501,692 | A | 3/1996 | Riza |
| 5,503,616 | A | 4/1996 | Jones |
| 5,505,686 | A | 4/1996 | Willis et al. |
| 5,507,755 | A | 4/1996 | Gresl et al. |
| 5,511,564 | A | 4/1996 | Wilk |
| 5,514,157 | A | 5/1996 | Nicholas et al. |
| 5,522,829 | A | 6/1996 | Michalos |
| 5,522,830 | A | 6/1996 | Aranyi |
| 5,527,321 | A | 6/1996 | Hinchliffe |
| 5,540,648 | A | 7/1996 | Yoon |
| 5,554,151 | A | 9/1996 | Hinchliffe |
| 5,555,883 | A | 9/1996 | Avitall |
| 5,558,133 | A | 9/1996 | Bortoli et al. |
| 5,562,693 | A | 10/1996 | Devlin et al. |
| 5,569,243 | A | 10/1996 | Kortenbach et al. |
| 5,569,298 | A | 10/1996 | Schnell |
| 5,573,540 | A | 11/1996 | Yoon |
| 5,578,030 | A | 11/1996 | Levin |
| 5,582,611 | A | 12/1996 | Tsuruta et al. |
| 5,582,617 | A | 12/1996 | Klieman et al. |
| 5,584,845 | A | 12/1996 | Hart |
| 5,591,179 | A | 1/1997 | Edelstein |
| 5,593,420 | A | 1/1997 | Eubanks, Jr. et al. |
| 5,595,562 | A | 1/1997 | Grier |
| 5,597,378 | A | 1/1997 | Jervis |
| 5,601,573 | A | 2/1997 | Fogelberg et al. |
| 5,601,588 | A | 2/1997 | Tonomura et al. |
| 5,604,531 | A | 2/1997 | Iddan et al. |
| 5,607,389 | A | 3/1997 | Edwards et al. |
| 5,607,450 | A | 3/1997 | Zvenyatsky et al. |
| 5,613,975 | A | 3/1997 | Christy |
| 5,618,303 | A | 4/1997 | Marlow et al. |
| 5,620,415 | A | 4/1997 | Lucey et al. |
| 5,624,399 | A | 4/1997 | Ackerman |
| 5,624,431 | A | 4/1997 | Gerry et al. |
| 5,628,732 | A | 5/1997 | Antoon, Jr. et al. |
| 5,630,782 | A | 5/1997 | Adair |
| 5,643,283 | A | 7/1997 | Younker |
| 5,643,292 | A | 7/1997 | Hart |
| 5,643,294 | A | 7/1997 | Tovey et al. |
| 5,644,798 | A | 7/1997 | Shah |
| 5,645,083 | A | 7/1997 | Essig et al. |
| 5,649,372 | A | 7/1997 | Souza |
| 5,653,677 | A | 8/1997 | Okada et al. |
| 5,653,722 | A | 8/1997 | Kieturakis |
| 5,662,663 | A | 9/1997 | Shallman |
| 5,669,875 | A | 9/1997 | van Eerdenburg |
| 5,681,324 | A | 10/1997 | Kammerer et al. |
| 5,681,330 | A | 10/1997 | Hughett et al. |
| 5,685,820 | A | 11/1997 | Riek et al. |
| 5,690,656 | A | 11/1997 | Cope et al. |
| 5,690,660 | A | 11/1997 | Kauker et al. |
| 5,695,448 | A | 12/1997 | Kimura et al. |
| 5,695,505 | A | 12/1997 | Yoon |
| 5,695,511 | A | 12/1997 | Cano et al. |
| 5,700,275 | A | 12/1997 | Bell et al. |
| 5,702,438 | A | 12/1997 | Avitall |
| 5,704,892 | A | 1/1998 | Adair |
| 5,709,708 | A | 1/1998 | Thal |
| 5,716,326 | A | 2/1998 | Dannan |
| 5,730,740 | A | 3/1998 | Wales et al. |
| 5,741,278 | A | 4/1998 | Stevens |
| 5,741,285 | A | 4/1998 | McBrayer et al. |
| 5,746,759 | A | 5/1998 | Meade et al. |
| 5,749,881 | A | 5/1998 | Sackier et al. |
| 5,749,889 | A | 5/1998 | Bacich et al. |
| 5,752,951 | A | 5/1998 | Yanik |
| 5,755,731 | A | 5/1998 | Grinberg |
| 5,766,167 | A | 6/1998 | Eggers et al. |
| 5,766,170 | A | 6/1998 | Eggers |
| 5,766,205 | A | 6/1998 | Zvenyatsky et al. |
| 5,769,849 | A | 6/1998 | Eggers |
| 5,779,701 | A | 7/1998 | McBrayer et al. |
| 5,779,716 | A | 7/1998 | Cano et al. |
| 5,779,727 | A | 7/1998 | Orejola |
| 5,782,859 | A | 7/1998 | Nicholas et al. |
| 5,782,866 | A | 7/1998 | Wenstrom, Jr. |
| 5,791,022 | A | 8/1998 | Bohman |
| 5,792,113 | A | 8/1998 | Kramer et al. |
| 5,792,153 | A | 8/1998 | Swain et al. |
| 5,792,165 | A | 8/1998 | Klieman et al. |
| 5,797,835 | A | 8/1998 | Green |
| 5,797,928 | A | 8/1998 | Kogasaka |
| 5,797,939 | A | 8/1998 | Yoon |
| 5,797,941 | A | 8/1998 | Schulze et al. |
| 5,803,903 | A | 9/1998 | Athas et al. |
| 5,808,665 | A | 9/1998 | Green |
| 5,810,806 | A | 9/1998 | Ritchart et al. |
| 5,810,849 | A | 9/1998 | Kontos |
| 5,810,865 | A | 9/1998 | Koscher et al. |
| 5,810,876 | A | 9/1998 | Kelleher |
| 5,810,877 | A | 9/1998 | Roth et al. |
| 5,813,976 | A | 9/1998 | Filipi et al. |
| 5,814,058 | A | 9/1998 | Carlson et al. |
| 5,817,061 | A | 10/1998 | Goodwin et al. |
| 5,817,107 | A | 10/1998 | Schaller |
| 5,817,119 | A | 10/1998 | Klieman et al. |
| 5,819,736 | A | 10/1998 | Avny et al. |
| 5,827,281 | A | 10/1998 | Levin |
| 5,827,299 | A | 10/1998 | Thomason et al. |
| 5,830,231 | A | 11/1998 | Geiges, Jr. |
| 5,833,700 | A | 11/1998 | Fogelberg et al. |
| 5,833,703 | A | 11/1998 | Manushakian |
| 5,843,017 | A | 12/1998 | Yoon |
| 5,849,022 | A | 12/1998 | Sakashita et al. |
| 5,853,374 | A | 12/1998 | Hart et al. |
| 5,855,585 | A | 1/1999 | Kontos |
| 5,860,913 | A | 1/1999 | Yamaya et al. |
| 5,860,995 | A | 1/1999 | Berkelaar |
| 5,868,762 | A | 2/1999 | Cragg et al. |
| 5,876,411 | A | 3/1999 | Kontos |
| 5,882,331 | A | 3/1999 | Sasaki |
| 5,882,344 | A | 3/1999 | Stouder, Jr. |
| 5,893,846 | A | 4/1999 | Bales et al. |
| 5,893,874 | A | 4/1999 | Bourque et al. |
| 5,893,875 | A | 4/1999 | O'Connor et al. |
| 5,899,919 | A | 5/1999 | Eubanks, Jr. et al. |
| 5,902,254 | A | 5/1999 | Magram |
| 5,904,702 | A | 5/1999 | Ek et al. |

(56) References Cited

U.S. PATENT DOCUMENTS

| | | |
|---|---|---|
| 5,908,420 A | 6/1999 | Parins et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,944,718 A | 8/1999 | Austin et al. |
| 5,951,549 A | 9/1999 | Richardson et al. |
| 5,954,720 A | 9/1999 | Wilson et al. |
| 5,954,731 A | 9/1999 | Yoon |
| 5,957,943 A | 9/1999 | Vaitekunas |
| 5,957,953 A | 9/1999 | DiPoto et al. |
| 5,971,995 A | 10/1999 | Rousseau |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,989,182 A | 11/1999 | Hori et al. |
| 5,993,447 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,033,399 A | 3/2000 | Gines |
| 6,053,927 A | 4/2000 | Hamas |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,108 A | 7/2000 | McBrayer et al. |
| 6,096,046 A | 8/2000 | Weiss |
| 6,102,926 A | 8/2000 | Tartaglia et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,139,555 A | 10/2000 | Hart et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,159,200 A | 12/2000 | Verdura et al. |
| 6,165,184 A | 12/2000 | Verdura et al. |
| 6,168,570 B1 | 1/2001 | Ferrera |
| 6,168,605 B1 | 1/2001 | Measamer et al. |
| 6,170,130 B1 | 1/2001 | Hamilton et al. |
| 6,179,776 B1 | 1/2001 | Adams et al. |
| 6,179,837 B1 | 1/2001 | Hooven |
| 6,183,420 B1 | 2/2001 | Douk et al. |
| 6,190,353 B1 * | 2/2001 | Makower et al. .......... 604/95.01 |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,214,007 B1 | 4/2001 | Anderson |
| 6,228,096 B1 | 5/2001 | Marchand |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,322,578 B1 | 11/2001 | Houle et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 * | 3/2002 | Cole ............................ 606/153 |
| 6,355,035 B1 | 3/2002 | Manushakian |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,391,029 B1 | 5/2002 | Hooven et al. |
| 6,402,735 B1 | 6/2002 | Langevin |
| 6,406,440 B1 | 6/2002 | Stefanchik |
| 6,409,733 B1 | 6/2002 | Conlon et al. |
| 6,431,500 B1 | 8/2002 | Jacobs et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,464,701 B1 | 10/2002 | Hooven et al. |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,503,192 B1 | 1/2003 | Ouchi |
| 6,506,190 B1 | 1/2003 | Walshe |
| 6,508,827 B1 | 1/2003 | Manhes |
| 6,543,456 B1 | 4/2003 | Freeman |
| 6,551,270 B1 | 4/2003 | Bimbo et al. |
| 6,554,829 B2 | 4/2003 | Schulze et al. |
| 6,558,384 B2 | 5/2003 | Mayenberger |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 * | 6/2003 | Makower ..................... 623/1.23 |
| 6,585,642 B2 | 7/2003 | Christopher |
| 6,585,717 B1 | 7/2003 | Wittenberger et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,620,193 B1 | 9/2003 | Lau et al. |
| 6,626,919 B1 | 9/2003 | Swanstrom |
| 6,632,229 B1 | 10/2003 | Yamanouchi |
| 6,638,286 B1 | 10/2003 | Burbank et al. |
| 6,652,521 B1 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |

(56) References Cited

U.S. PATENT DOCUMENTS

| | | |
|---|---|---|
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,884,213 B2 | 4/2005 | Raz et al. |
| 6,887,255 B2 | 5/2005 | Shimm |
| 6,896,683 B1 | 5/2005 | Gadberry et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,629 B2 | 8/2006 | Weller et al. |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,195,612 B2 | 3/2007 | Van Sloten et al. |
| 7,195,631 B2 | 3/2007 | Dumbauld |
| 7,208,005 B2 | 4/2007 | Frecker et al. |
| 7,211,092 B2 | 5/2007 | Hughett |
| 7,223,272 B2 | 5/2007 | Francese et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,252,660 B2 | 8/2007 | Kunz |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,322 B2 | 7/2008 | Wenchell |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,488,295 B2 | 2/2009 | Burbank et al. |

(56) References Cited

U.S. PATENT DOCUMENTS

| | | |
|---|---|---|
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,618,398 B2 | 11/2009 | Holman et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,713,270 B2 | 5/2010 | Suzuki |
| 7,736,374 B2 | 6/2010 | Vaughan et al. |
| 7,762,998 B2 | 7/2010 | Birk et al. |
| 7,771,416 B2 | 8/2010 | Spivey et al. |
| 7,780,683 B2 | 8/2010 | Roue et al. |
| 7,794,475 B2 | 9/2010 | Hess et al. |
| 7,837,615 B2 | 11/2010 | Le et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,896,887 B2 | 3/2011 | Rimbaugh et al. |
| 7,918,869 B2 | 4/2011 | Saadat et al. |
| 7,931,624 B2 | 4/2011 | Smith et al. |
| 7,947,000 B2 | 5/2011 | Vargas et al. |
| 7,955,298 B2 | 6/2011 | Carroll et al. |
| 7,963,975 B2 | 6/2011 | Criscuolo |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114732 A1 | 6/2003 | Webler et al. |
| 2003/0120257 A1 | 6/2003 | Houston et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |

(56) References Cited

U.S. PATENT DOCUMENTS

| | | |
|---|---|---|
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0069396 A1 | 3/2006 | Meade et al. |
| 2006/0069424 A1 | 3/2006 | Acosta et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247576 A1 | 11/2006 | Poncet |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1* | 12/2006 | Cole et al. ............... 606/153 |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0015965 A1 | 1/2007 | Cox et al. |
| 2007/0016225 A1 | 1/2007 | Nakao |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0142706 A1 | 6/2007 | Matsui et al. |
| 2007/0156127 A1 | 7/2007 | Rioux et al. |
| 2007/0161855 A1 | 7/2007 | Mikkaichi et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203487 A1 | 8/2007 | Sugita |
| 2007/0208364 A1 | 9/2007 | Smith et al. |
| 2007/0213754 A1 | 9/2007 | Mikkaichi et al. |

(56) References Cited

U.S. PATENT DOCUMENTS

| | | |
|---|---|---|
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260273 A1 | 11/2007 | Cropper et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282371 A1 | 12/2007 | Lee et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015552 A1 | 1/2008 | Doyle et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0147113 A1 | 6/2008 | Nobis et al. |
| 2008/0171907 A1 | 7/2008 | Long et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0198231 A1 | 8/2009 | Esser et al. |
| 2009/0227828 A1 | 9/2009 | Swain et al. |
| 2009/0248055 A1 | 10/2009 | Spivey et al. |
| 2009/0281559 A1 | 11/2009 | Swain et al. |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0249700 A1 | 9/2010 | Spivey |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |

(56) References Cited

U.S. PATENT DOCUMENTS

| | | | |
|---|---|---|---|
| 2011/0105850 A1 | 5/2011 | Voegele et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |

FOREIGN PATENT DOCUMENTS

| | | |
|---|---|---|
| DE | 4323585 A1 | 1/1995 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 1769749 B1 | 11/2009 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 8-29699 A | 2/1996 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/101075 A2 | 8/2008 |
| WO | WO 2008/102154 A2 | 8/2008 |
| WO | WO 2009/021030 A2 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A2 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

Ethicon, Inc., "Wound Closure Manual: Chapter 3 (The Surgical Needle)," 15 pages, (publication date unknown).

(56) References Cited

OTHER PUBLICATIONS

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col. Rectum, (1985), vol. 28, pp. 484-490.

P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview &navRelId=1000.1003&method=D . . . , accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
U.S. Appl. No. 12/019,461, filed Jan. 24, 2008.
U.S. Appl. No. 12/045,318, filed Mar. 10, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 12/060,601, filed Apr. 1, 2008.

(56) References Cited

OTHER PUBLICATIONS

U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/359,824, filed Jan. 26, 2009.
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM),"EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al,, "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al,, "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.

\* cited by examiner

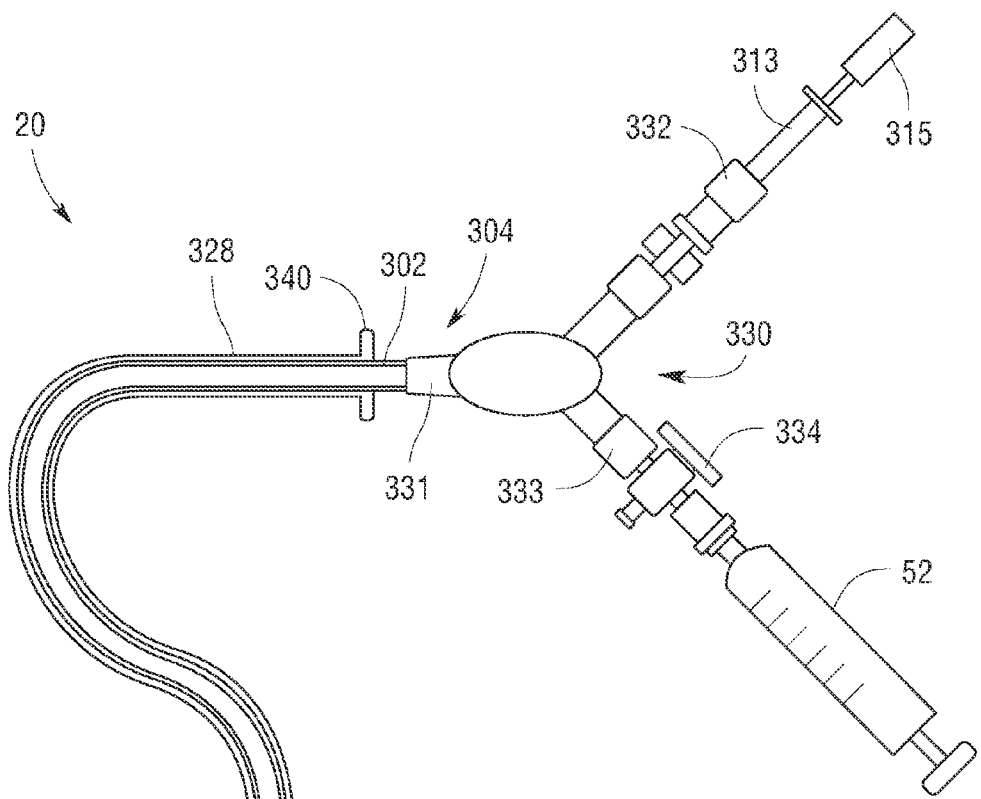
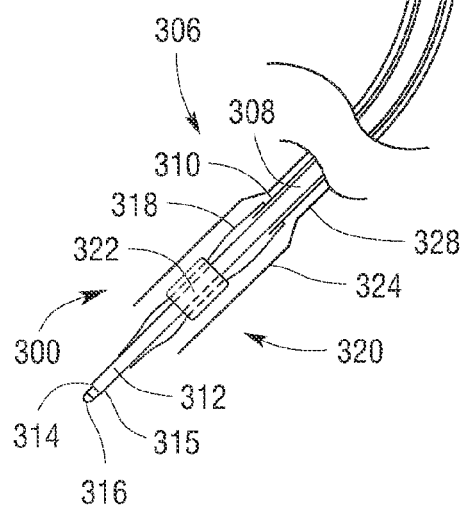
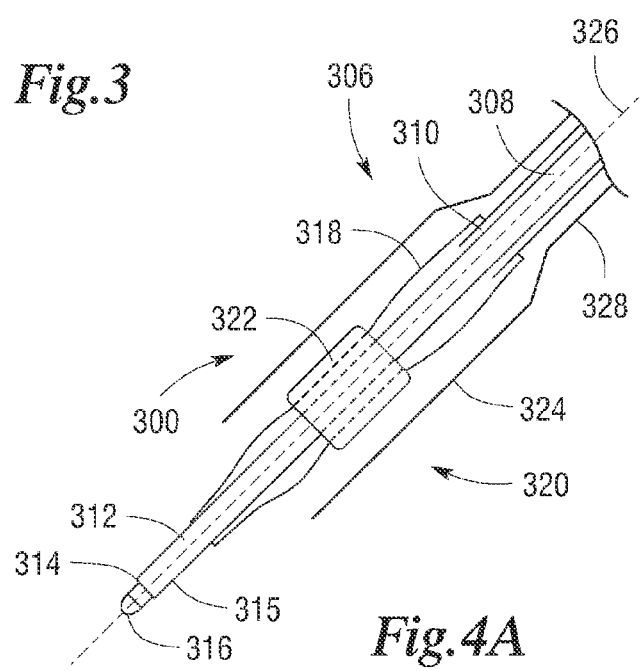
Fig.3
Fig.4A

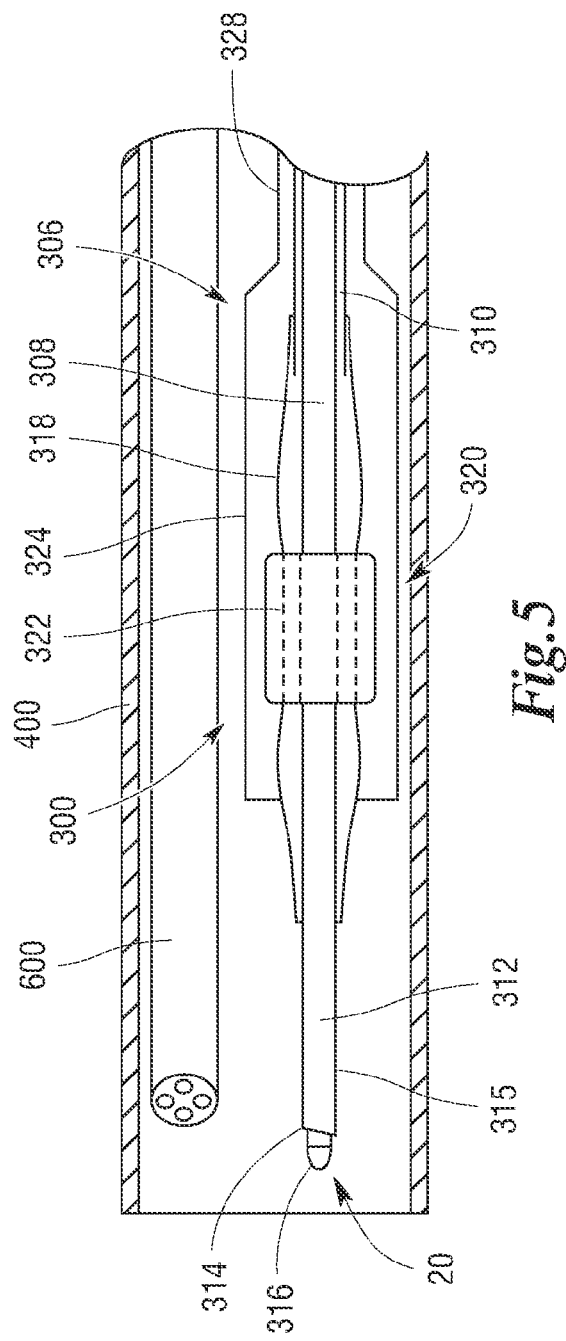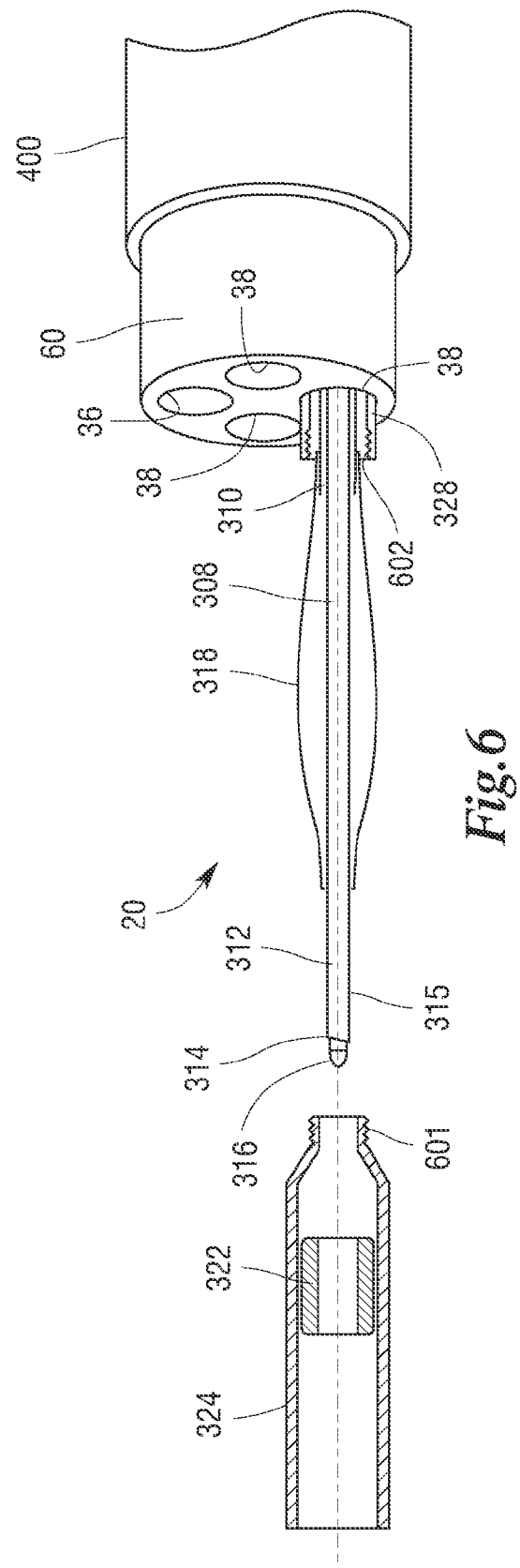

APPARATUS FOR FORMING AN ANASTOMOSIS

BACKGROUND

The present application relates, in general, to surgical devices for forming an anastomosis between internal body lumens and, more particularly, to devices that can be inserted through a natural orifice in the body and used to form an anastomosis between various gastrointestinal lumens.

Access to the abdominal cavity may be required for diagnostic and therapeutic endeavors for a variety of medical and surgical diseases. Historically, abdominal access has required a formal laparotomy to provide adequate exposure. Such procedures, which require incisions to be made in the abdomen, are not particularly well-suited for patients that may have extensive abdominal scarring from previous procedures, those persons who are morbidly obese, those individuals with abdominal wall infection, and those patients with diminished abdominal wall integrity, such as patients with burns and skin grafting. Other patients simply do not want to have a scar if it can be avoided.

Minimally invasive procedures are desirable because such procedures can reduce pain and provide relatively quick recovery times as compared with conventional open medical procedures. Many minimally invasive procedures are performed with an endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall. The trocar must pass through several layers of overlapping tissue/muscle before reaching the abdominal cavity.

Still less invasive treatments include those that are performed through insertion of an endoscope through a natural body orifice to a treatment region. Examples of this approach include, but are not limited to a gastro-jejunostomy, jejuno-jejunostomy, cholecystectomy, appendectomy, cystoscopy, hysteroscopy, esophagogastroduodenoscopy, and colonoscopy. Many of these procedures employ the use of a flexible endoscope during the procedure. Flexible endoscopes often have a flexible, steerable articulating section near the distal end that can be controlled by the user by utilizing controls at the proximal end. Minimally invasive therapeutic procedures to treat diseased tissue by introducing medical instruments to a tissue treatment region through a natural opening of the patient (e.g., mouth, anus, vagina) are known as Natural Orifice Translumenal Endoscopic Surgery (NOTES)™ procedures. Medical instruments such as endoscopic needles may be introduced through the working channel of a flexible endoscope, which typically has a diameter in the range of approximately 2.5 millimeters ("mm") (or approximately 0.10 inches ("in")) to approximately 4.0 mm (or approximately 0.16 in).

These minimally invasive surgical procedures have changed some of the major open surgical procedures such as gastro-jejunostomy or jejuno-jejunostomy, to simple outpatient surgery. Consequently, the patient's recovery time has changed from weeks to days. These types of surgeries are often used for creating an anastomosis between the stomach and the jejunum and/or between a portion of the jejunum and another portion of the jejunum.

In the past, such surgical procedures were also employed to address various problems occurring in the jejunum (a portion of the small intestine). For example, such procedures were commonly employed to address blockages or strictures in the jejunum or to address diseases occurring therein. In some situations, it becomes necessary to create a gastro-jejunostomy—an anastomosis between the stomach and the jejunum—or a jejuno-jejunostomy—an anastomosis between one portion of the jejunum and another portion of the jejunum. In addition to suffering from the above-mentioned limitations, current laparoscopic and endoscopic surgical techniques also fail to provide a convenient way for inserting a distal mass and are generally incapable of applying sufficient mass and force to effect a clinically acceptable compression anastomosis.

Consequently a significant need exists for an alternative to conventional surgery that eliminates abdominal incisions and incision-related complications by employing an endoscopic technique to treat an abdominal pathology.

There is a further need for a surgical device that can be introduced into the stomach through the mouth and used to form a clinically acceptable compression anastomosis between the stomach and the jejunum and/or a portion of the jejunum and another portion of the jejunum.

The foregoing discussion is intended only to illustrate some of the shortcomings present in the field of the invention at the time, and should not be taken as a disavowal of claim scope.

FIGURES

The novel features of the various embodiments are set forth with particularity in the appended claims. The various embodiments, however, both as to organization and methods of operation, may be best understood by reference to the following description, taken in conjunction with the accompanying drawings as follows.

FIG. 3 illustrates one embodiment of a surgical instrument.

FIG. 4A is a cross-sectional view of a distal portion of the surgical instrument of FIG. 3.

FIG. 5 is a cross-sectional view of the distal portion of the surgical instrument embodiment depicted in FIG. 4A contained within an over-tube.

FIG. 6 is a cross-sectional view of the distal portion of the surgical instrument embodiment depicted in FIG. 4A extending from an endoscope.

DESCRIPTION

Before explaining the various embodiments in detail, it should be noted that the embodiments are not limited in their application or use to the details of construction and arrangement of parts illustrated in the accompanying drawings and description. The illustrative embodiments may be implemented or incorporated in other embodiments, variations and modifications, and may be practiced or carried out in various ways. For example, the surgical instrument configurations disclosed below are illustrative only and not meant to limit the scope or application thereof. Furthermore, unless otherwise indicated, the terms and expressions employed herein have been chosen for the purpose of describing the illustrative embodiments for the convenience of the reader and not to limit the scope thereof.

Newer procedures have developed which may even be less invasive than the laparoscopic procedures used in earlier surgical procedures. Many of these procedures employ the use of a flexible endoscope during the procedure. Flexible endoscopes often have a flexible, steerable articulating section near the distal end that can be controlled by the user by utilizing controls at the proximal end. Minimally invasive therapeutic procedures to treat diseased tissue by introducing medical instruments to a tissue treatment region through a natural opening of the patient are known as NOTES™. NOTES™ is a surgical technique whereby operations can be performed trans-orally (as depicted in FIG. 1), trans-anally, and/or trans-vaginally.

Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined with the features of other embodiments without limitation, and modifications and variations are intended to be included within the scope of the claims.

It will be appreciated that the terms "proximal" and "distal" are used herein with reference to a clinician gripping the surgical instrument. Thus, magnet placement assemblies are distal with respect to the handle assemblies of the surgical instrument. It will be further appreciated that, for convenience and clarity, spatial terms such as "top" and "bottom" also are used herein with respect to the clinician gripping the handle. However, surgical instruments may be used in many orientations and positions, and these terms are not intended to be limiting and absolute.

Figure 1:
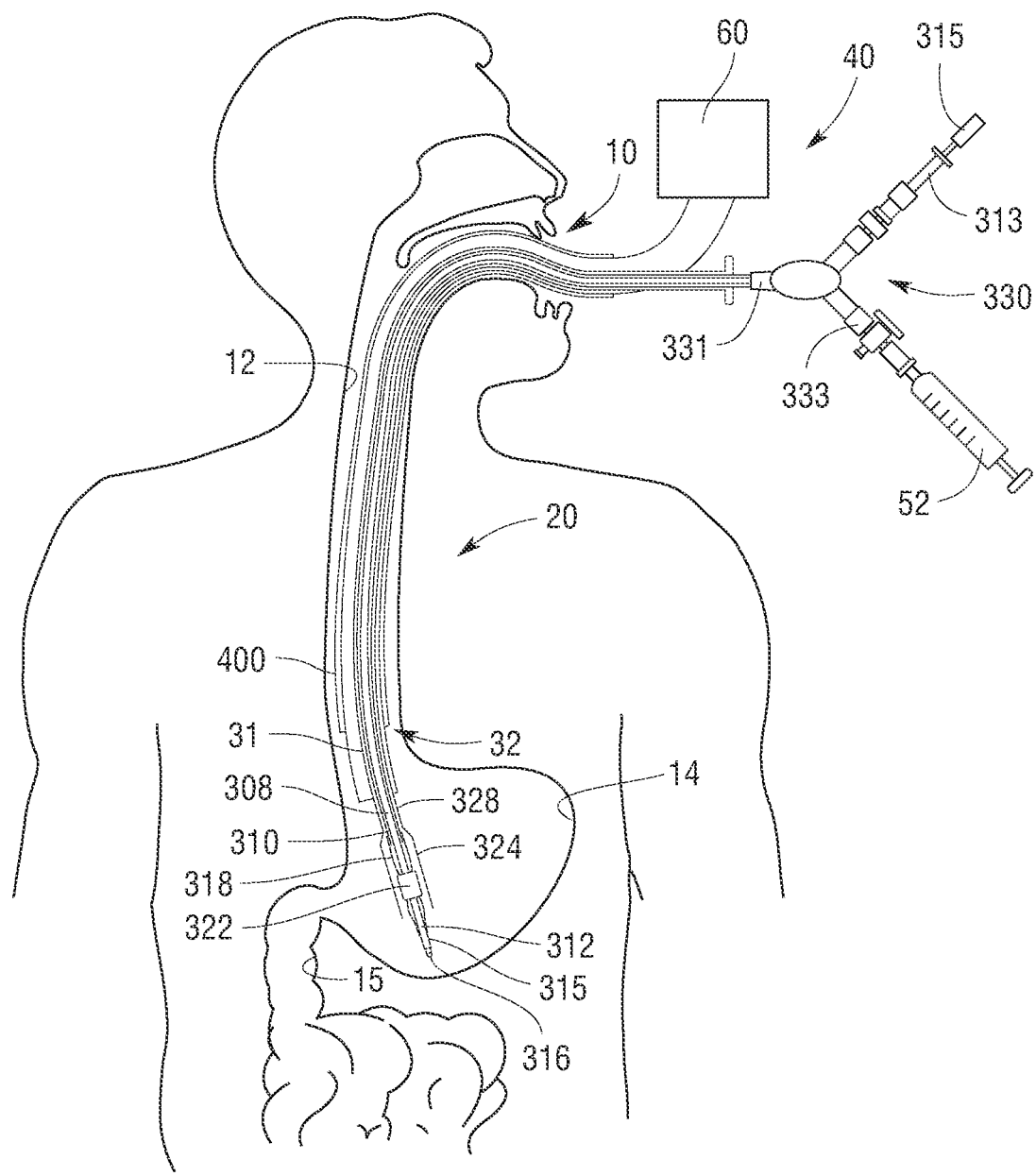
FIG. 1 illustrates the use of one embodiment of a surgical instrument inserted through a patient's mouth and esophagus to create an anastomosis between the stomach and the jejunum and/or between a portion of the jejunum and another portion of the jejunum.

FIG. 1 illustrates the use of one embodiment of a surgical instrument 20 inserted through a patient's mouth 10 and esophagus 12 to create an anastomosis between the stomach 14 and the jejunum 15 and/or between a portion of the jejunum 15 and another portion of the jejunum 15. The surgical instrument of FIG. 1 may comprise a flexible endoscopic portion 31 which may be inserted into the upper gastrointestinal tract of the patient. FIG. 1 illustrates, in general form, one embodiment of the surgical instrument 20 that can be inserted through a natural orifice such as the mouth 10 and esophagus 12 into the stomach 14 to establish a surgical opening in the stomach 14 for performing a surgical operation such as a gastro-jejunostomy or jejuno-jejunostomy.

Figure 2:
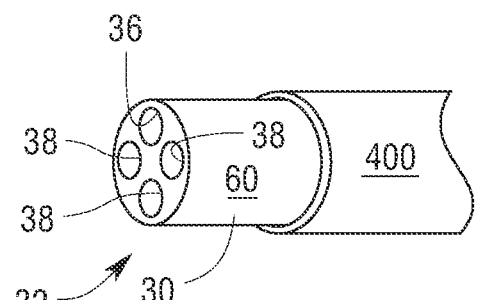
FIG. 2 is partial perspective view of a portion of an endoscope.

FIG. 2 is a drawing of the distal end 32 of an endoscope. As shown in FIG. 2, the endoscope 60 may comprise a hollow outer sleeve 30 that has a distal end 32 and a proximal end 40 (FIG. 1). In various embodiments, the hollow outer sleeve 30 may be fabricated from, for example, nylon or high density polyethylene plastic. In various embodiments, the hollow outer sleeve 30 can serve to define various tool-receiving passages referred to as working channels 38 that extend from the natural orifice 10 to the surgical site. An endoscope 60 (FIG. 1) may be used for viewing a surgical site within the patient's body by way of a viewing port 36. Various cameras and/or lighting apparatuses may be inserted into the viewing port 36 of the endoscope 60 to provide the surgeon with a view of the surgical site.

FIG. 3 illustrates one embodiment of the surgical instrument 20. FIG. 4A is a cross-sectional view of a distal portion 300 of the surgical instrument 20. As shown in FIG. 3, the surgical instrument 20 may comprise a first catheter 302 with a proximal end 304 and a distal end 306. The surgical instrument 20 may be configured to flexibly extend through the working channel 38 of the endoscope 60 along the length of the endoscope 60 from the proximal end 40 to the distal end 32 (FIG. 1). The surgical instrument 20 may be flexible to allow the surgical instrument 20 to move along the gastrointestinal tract.

In one embodiment, the first catheter 302 may comprise a first opening 308 and a second opening 310. The first opening 308 and the second opening 310 may comprise hollow channels that extend from the proximal end 304 of the catheter 302 to the distal end 306 of the catheter 302. The first opening 308 may be configured to slidably receive a hole-forming instrument 312 from the proximal end 304 to the distal end 306. The first catheter 302 may be fabricated from nylon, polyvinyl-chloride (PVC), urethane, or any other suitable polymer. The hole-forming instrument 312 may comprise a surgical needle. In one embodiment, the hole-forming instrument 312 may comprise a rotary needle. Various embodiments of a rotary needle are described in U.S. patent application Ser. No. 12/359,824, entitled "Rotary Needle for Natural Orifice Translumenal Endoscopic Surgery," now U.S. Patent Application Publication No. 2010/0191267, which is incorporated herein by reference in its entirety. The hole-forming instrument 312 may be rotatable by rotating a proximal portion 313 of the hole-forming instrument 312 to penetrate tissue at a distal end 315 of the hole-forming instrument 312. In various embodiments, the hole-forming instrument 312, or needle, may be formed of a tube which may have a channel extending from a proximal end of the hole-forming instrument 312 to the distal end 315 of the hole-forming instrument 312. The movement of the hole-forming instrument 312 may be controlled by the operator of the surgical instrument 20 through the use of the proximal portion 313. The proximal portion 313 may be translated distally in the direction shown by arrow A, translated proximally in the direction of arrow B, and/or rotated either clockwise or counter-clockwise by the operator of the surgical instrument 20 in the direction of arrow C.

In one embodiment, the hole-forming instrument 312 may be hollow. The distal end 315 of the hole-forming instrument 312 may comprise a tissue penetrating tip 314. As shown in FIG. 4A, the tissue-penetrating tip 314 may be located at the distal end 315 at the outside of the diameter of the hole-forming instrument 312. In one embodiment, the tissue penetrating tip 314 may be chamfered around a periphery of the hole-forming instrument 312 at the distal end 315 of the hole-forming instrument 312. In one embodiment, the tissue penetrating tip 314 may be formed such that the hole-forming instrument 312 is cut at an angle. The tissue penetrating tip 314 may be cut and/or ground so that the sharp portion of the tissue penetrating tip 314 is located at the outer edge of the diameter of the hole-forming instrument 312. The hole-forming instrument 312 may be ground to form the tissue penetrating tip 314. The hole-forming instrument 312 may be fabricated from medical grade stainless steel, nitinol, or polyetheretherketon (PEEK) hypodermic tubing or any other suitable medical grade material which may include metal and/or plastic suitable for medical applications, for example. Alternatively, the hole-forming instrument 312 may be formed of a tube fabricated from an alternate type of metallic or polymeric material and attached to a cannulated needle, or tube, (not shown), such as by bolting, screwing, welding, crimping, gluing, brazing, soldering, press fitting, riveting, heat shrinking, heat welding, ultrasonic welding, or any other suitable method. The hole-forming instrument 312 may have an outer diameter in the range of approximately 0.25 mm (or approximately 0.010 in) to approximately 2.05 mm (or approximately 0.080 in). For example, the hole-forming instrument 312 may be formed from medical grade stainless steel hypodermic tubing having an outer diameter of approximately 0.90 mm (or approximately 0.035 in). The hole-forming instrument 312 may have an inner diameter in the range of approximately 0.13 mm (or approximately 0.005 in) to approximately 1.14 mm (or approximately 0.045 in). For example, the hole-forming instrument 312 may have an inner diameter of approximately 0.50 mm (or approximately 0.020 in).

In one embodiment, the surgical instrument 20 may comprise a guide wire 316. The guide wire 316 may be configured to be slidably disposed within the hole-forming instrument 312. The guide wire 316 may extend from the proximal end 304 to the distal end 306 of the first catheter 302. The guide wire 316 may be fabricated from a shape memory alloy formed of nickel titanium (NiTi) commonly referred to as nitinol, or any other suitable material, with a TEFLON®, or any other suitable coating, placed upon the guide wire 316. In various embodiments, the distal end of the guide wire 316 may be formed with a blunt tip to prevent the guide wire 316 from puncturing tissue of the patient in undesired locations. The guide wire 316 may be flexible enough to travel along the length of the surgical instrument 20 (FIG. 1). The operator may control the guide wire 316 from the proximal end of the surgical instrument 20. The guide wire 316 may be controlled by the operator through the use of a guide wire handle 317. The operator may have the ability to extend the guide wire 316, or to move the guide wire 316 distally, by pushing the guide wire handle 317. In addition, the operator may have the ability to retract the guide wire 316, or move the guide wire 316 proximally, by pulling the guide wire handle 317.

The first catheter 302 may further comprise an inflatable member 318. The inflatable member 318 may be located near the distal end 306 of the first catheter 302. The inflatable member 318 may be in fluid communication with the second opening 310. As used herein, the term "fluid communication" means that the elements are coupled together with an appropriate opening, lumen, supply passage, line or other means to permit the passage of fluid (air, water, saline) therebetween. The second opening 310 may be coupled to a fluid source. In one embodiment, the fluid source may be a syringe 52, as shown in FIG. 3, which may comprise a source of water, saline solution, air, and/or any other suitable fluid. In various embodiments, the inflatable member 318 may be fabricated from silicone or latex rubber, or a variety of other elastomers and may be attached to the second opening 310 by, for example, suitable adhesive such as cyanoacrylate or epoxy glues, heat seal or light activated adhesives such that a substantially fluid tight seal is established between the second opening 310 and the inflatable member 318. In other embodiments, the inflatable member 318 may be fabricated from a material that is not substantially expandable, such as nylon, polyester or polyethylene terephthalate (PET), or a variety of other polymers, but nevertheless is sized to inflate into a desired shape as will be further described below.

Figure 4B:
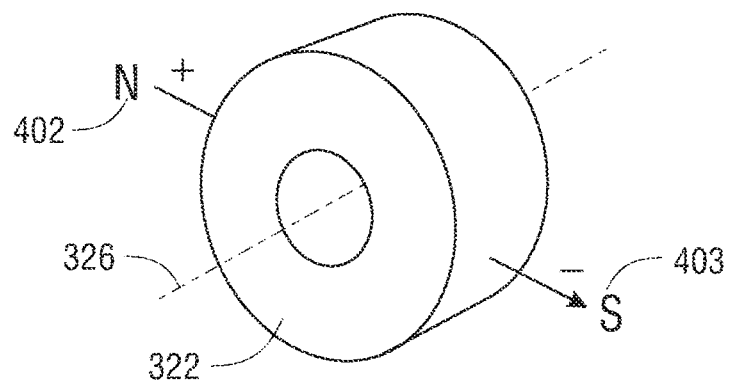
FIG. 4B is a perspective view of a diametrically magnetized cylindrical magnet.
Figure 4C:
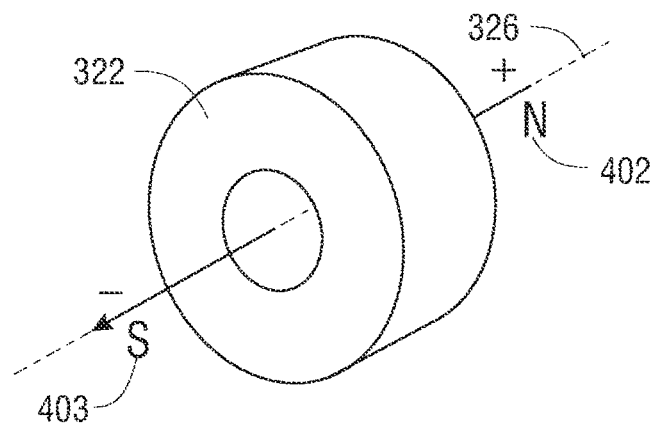
FIG. 4C is a perspective view of an axially magnetized cylindrical magnet.

In various embodiments, the assembly at the distal end of the surgical instrument 20 may comprise a magnet placement assembly 320. The magnet placement assembly 320 may comprise the hole-forming instrument 312, the guide wire 316, the inflatable member 318, a magnet 322, and an outer sleeve 324. FIG. 4B is a cross-sectional view of the magnet 322 where the magnet 322 is diametrically magnetized. FIG. 4C is a cross-sectional view of the magnet 322 where the magnet 322 is axially magnetized. The magnet 322 may have a cylindrical body. The cylindrical body may define an opening along an axis 326 of the cylindrical body. In one embodiment, as shown in FIG. 4B, the magnet 322 may be diametrically polarized such that the magnetic attraction occurs perpendicular to the axis 326 of the cylindrical body. The magnet 322, which may be diametrically magnetized, may have a north magnetic pole 402 and a south magnetic pole 403 arranged as shown in FIG. 4B. In one embodiment, as shown in FIG. 4C, the magnet 322 may be axially polarized such that the magnetic attraction occurs parallel to the axis 326 of the cylindrical body. The magnet 322, which may be axially polarized, may have the north magnetic pole 402 and the south magnetic pole 403 arranged as shown in FIG. 4C.

In one embodiment, the outer sleeve 324 may be hollow. The outer sleeve 324 may be configured to retain at least a portion of the inflatable member 318, the guide wire 316, the hole-forming instrument 312, and the magnet 322. The outer sleeve 324 may be attached to a second catheter 328. The outer sleeve 324 may be attached to the second catheter 328 by bolting, screwing, welding, crimping, gluing, brazing, soldering, press fitting, riveting, heat shrinking, heat welding, ultrasonic welding, or any other suitable method. The second catheter 328 may be configured to slidably retain the first catheter 302. The second catheter 328 may extend from the proximal end 304 of the first catheter 302 to the distal end 306 of the first catheter 302. The second catheter 328 may be fabricated from nylon, polyvinylchloride (PVC), urethane, or any other suitable polymer. The operator of the surgical instrument 20 may extend and/or retract the second catheter 318 to translate the outer sleeve 324. For example, the second catheter 328 may be extended distally to cause the outer sleeve 324 to contain the inflatable member 318 and then may be retracted proximally to completely expose the inflatable member 318. The second catheter 328 may be translated using a handle 340 located at the proximal end of the second catheter 328.

In one embodiment, the surgical instrument 20 may further comprise a Y-portion 330. The Y-portion 330 may comprise a first portion 331, a second portion 332, and a third portion 333. The first portion 331 of the Y-portion 330 may be connected to the proximal end 304 of the first catheter 302. The first portion 331 may be connected to the proximal end 304 by bolting, screwing, welding, crimping, gluing, brazing, soldering, press fitting, riveting, heat shrinking, heat welding, ultrasonic welding, or any other suitable method. The second portion 332 of the Y-portion 330 may be in communication with the first opening 308. The hole-forming instrument 312 and the handle portion 313 and/or the guide wire 316 and the handle portion 317 may extend from the second portion 332 near the proximal end of the surgical instrument 20. The third portion 333 of the Y-portion 330 may be in fluid communication with the second opening 310. The third portion 333 may be configured to receive the syringe 52, or any other fluid supply and/or vacuum device, at the proximal end of the surgical instrument. The second opening 310 may be adapted for fluid communication with the syringe 52, or any other fluid supply and/or vacuum device. The third portion 333 may comprise a valve 334. The valve 334 may be used to secure the fluid within the second opening 310 once the fluid has been supplied by the syringe 52, or the valve may be used to prevent the second opening 310 from receiving any fluid from the syringe 52.

FIG. 5 is a cross-sectional view of the distal portion of the surgical instrument 20 contained within an over-tube 400. In the embodiments shown in FIG. 5, the surgical instrument 20 may be used in conjunction with the over-tube 400. The over-tube 400 may be employed to allow various surgical instruments to be inserted into the body of a patient without each individual surgical instrument rubbing on the esophagus 12 (FIG. 1) of the patient. When the over-tube 400 is used, the over-tube 400 is advanced through the patient's esophagus 12 and, once in place at a desirable location, the individual surgical instruments are inserted and removed from the over-tube 400, thus rubbing on the inner wall of the over-tube 400 and not the esophagus 12 of the patient. The surgical instrument 20 may be inserted into the over-tube 400 with an additional endoscope 600 to allow viewing of the surgical site by the surgeon. The endoscope 600 may be of a smaller size than the endoscope used in conventional applications as it must fit within the over-tube 400 along with the surgical instrument 20. For example, the over-tube 400 may be formed of a tube with an inner diameter of approximately 14 mm (or approximately 0.55 in) and an outer diameter typically no greater than approximately 22 mm (or approximately 0.9 in), and the surgical instrument 20 may have a diameter of approximately 13 mm (or approximately 0.51 in). In order to fit within the over-tube 400 to provide the viewing of the surgical site, the endoscope 600 typically should have a diameter in the range of approximately 3 mm (or approximately 0.12 in) to approximately 14 mm (or approximately 0.55 in).

FIG. 6 is a cross-sectional view of the distal portion of the surgical instrument 20 extending from the endoscope 60. In one embodiment, as shown in FIG. 6, the surgical instrument 20 may be inserted through one of the working channels 38 of the endoscope 60. In order to be employed through the working channel 38 of the endoscope 60, the outer sleeve 324 may be "front-loaded" onto the distal end of the surgical instrument 20. This front-loading may be helpful due to the size of the outer sleeve 324. The outer sleeve 324 may have a diameter of approximately 20 mm (or approximately 0.80 in), but the working channel 38 may only have diameters in the range of approximately 2 mm (or approximately 0.08 in) to approximately 6 mm (or approximately 0.25 in). To be used in this configuration, the surgical instrument 20 may be inserted in the working channel 38 of the endoscope 60 without the outer sleeve 324 attached. Once a portion of the second catheter 328 of the surgical instrument 20 is extended distally from the working channel 38 of the endoscope 60, the outer sleeve 324 may be attached to the second catheter 328. As previously discussed, the outer sleeve 324 may be attached to the second catheter 328 by bolting, screwing, welding, crimping, gluing, brazing, soldering, press fitting, riveting, heat shrinking, heat welding, ultrasonic welding, or any other suitable method. In one embodiment, the outer sleeve 324 may be attached to the second catheter 328 by screwing outer sleeve male threads 601 onto second catheter female threaded portion 602. In addition, the magnet 322 may be placed on the inflatable member 318 after inserting the surgical instrument 20 into the endoscope 60. In one embodiment, the magnet 322 may be placed on the inflatable member 318 from the distal end 306 of the surgical instrument 20 after the surgical instrument 20 has extended from the working channel 38 of the endoscope 60.

Figure 7:
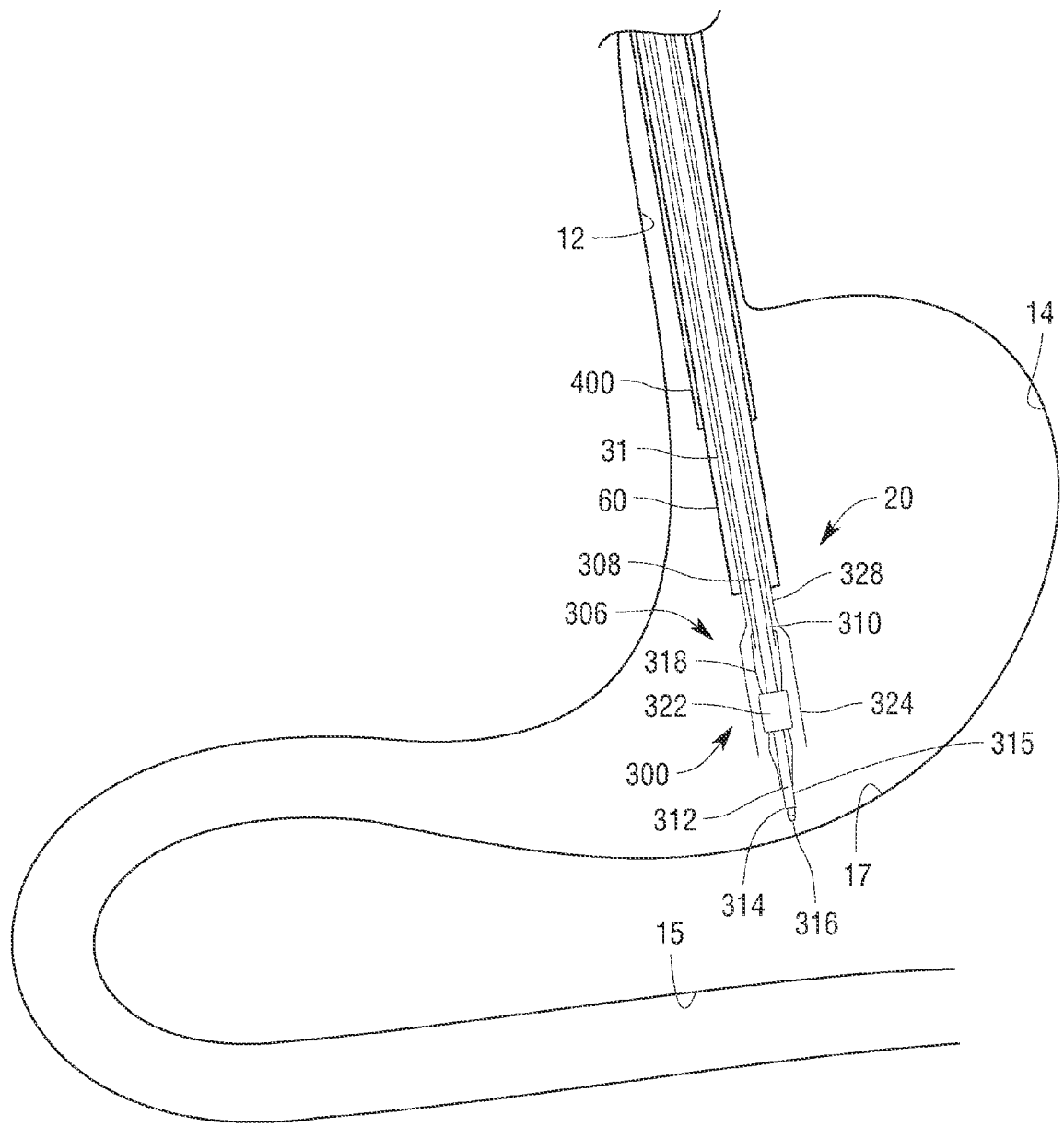
FIG. 7 is a diagrammatical view of a portion of the patient's gastrointestinal tract depicted in FIG. 1 wherein the surgical instrument of FIG. 3 has been inserted through the esophagus to puncture through a portion of the stomach wall.

FIG. 7 is another diagrammatical view of the patient's esophagus 12, stomach 14, and jejunum 15 depicted in FIG. 1, wherein the surgical instrument 20 has been inserted through the esophagus 12 to puncture through a portion 17 of the stomach 14 wall. The surgical instrument 20 depicted in FIG. 7 is shown with the magnet placement assembly 320 already loaded. The magnet placement assembly 320 may be loaded by placing the magnet 322 over the magnet placement assembly 320. The magnet 322 may be placed such that the hole-forming instrument 312, the guide wire 316, and the inflatable member 318 are inserted into the opening along the axis 326 of the magnet 322. The magnet 322 may be positioned along the length of the inflatable member 318 so that the magnet 322 may be placed approximately at the mid-point of the inflatable member 318. The outer sleeve 324 may be configured to retain at least a portion of the hole-forming instrument 312, the guide wire 316, the inflatable member 318, and the magnet 322. In various embodiments, the magnet 322 may be fabricated from magnet material such as Neodymium or other rare or earth ferrite materials magnetic materials, which may be optionally shrouded with plastic or rubber or any other suitable bio-compatible material.

As previously discussed, the surgical instrument 20 may be inserted trans-orally into the esophagus 12 of the patient. The surgical instrument 20 may extend into the stomach 14 of the patient. As shown in FIG. 7, the surgical instrument 20 may be extended until it contacts a portion 17 of the stomach 14 wall. Although depicted as forming an anastomis between a first portion and a second portion of the jejunum 15, the surgical instrument 20 may be used to form an anastomis between any two body lumens, which may include different or the same body lumen, for example, a gastro-jejunostomy or jejuno-jejunostomy. The body lumens may comprise any internal body lumens, or portion thereof, which may include the stomach 14, the jejunum 15 or another portion of the small intestine, the large intestine, the esophagus 12, and/or any other body lumen.

Figure 8:
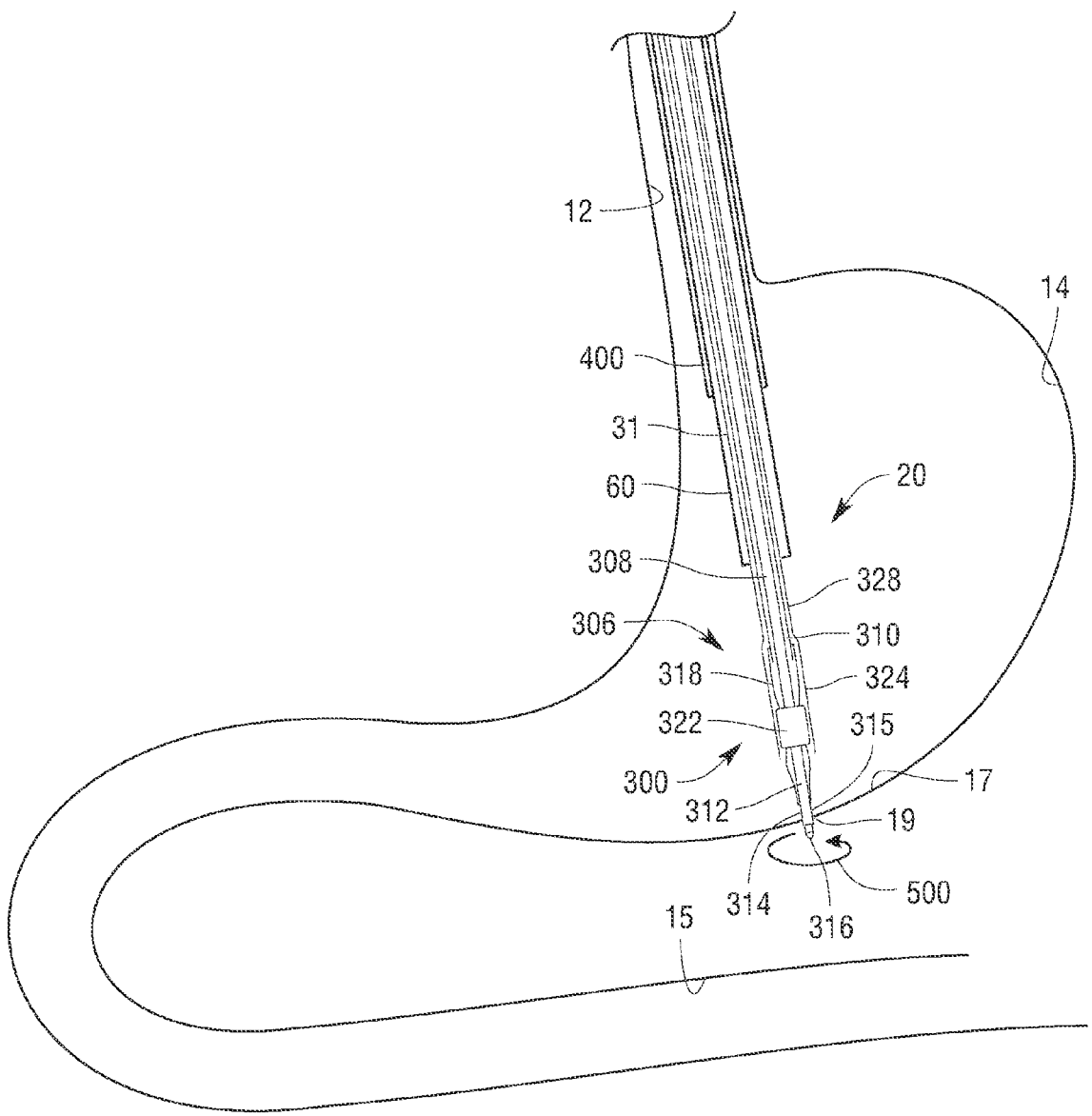
FIG. 8 is another diagrammatical view of a portion of the patient's gastrointestinal tract depicted in FIG. 7, wherein a hole-forming instrument has punctured a portion of the stomach wall.

FIG. 8 is another diagrammatical view of the patient's esophagus 12, stomach 14, and jejunum 15 depicted in FIG. 7, wherein a hole-forming instrument 312 has punctured a portion 17 of the stomach 14 wall. As shown in FIG. 8, the hole forming instrument 312 may form an opening 19 in the portion 17 of the stomach 14 wall. In one embodiment, the hole-forming instrument 312 may comprise a rotary needle which may be rotatable by rotating a proximal portion 313 of the hole-forming instrument 312 to penetrate tissue at a distal end 315 of the hole-forming instrument 312 (FIG. 3). The rotation of the rotary needle is depicted by arrow 500. In one embodiment, the hole-forming instrument 312 may puncture the portion 17 of the stomach 14 wall without rotation.

In one embodiment, the magnet placement device 320 may be located through the opening 19. Prior to locating the magnet placement device 320 through the opening 19, the inflatable member 318 may be inflated. The inflation of the inflatable member 318 may create a contiguous surface along the outside of the magnet placement assembly 320. The outer sleeve 324 may be used to eliminate the "pillowing" effect that may occur without the outer sleeve 324. For example, if a surgeon attempts to inflate the inflatable member 318 without an outer sleeve 324 in place, the "pillowing" effect may occur where there is a slight recess in the inflatable member 318 at the distal end of the magnet 322 where the inflatable member 318 may slide through the opening in the inner diameter of the magnet 322 thus creating a "pillowing" effect. Where the inflatable member 318 exits the inner diameter of the magnet 322 at the proximal end of the magnet 322, another "pillowing" effect may occur where the inflatable member 318 may exit the inner diameter of the magnet 322. This may create a dual pillow inflatable member 318, which may be hard to locate, or push, through the tissue because as a surgeon starts pushing the inflatable member 318 through the tissue, the tissue may come in contact with the distal edge of the magnet 322 and, thus, not advance smoothly through the opening 19. The outer sleeve 324 used in conjunction with the at least partially inflated inflatable member 318 may create a contiguous smooth surface that can be easily pushed through the wall of the tissue, for example, through the opening 19 in the portion 17 of the stomach 14 wall. This configuration may create a tapered dilated distal end that allows a surgeon to locate the magnet placement assembly 320 through the opening 19 in the portion 17 of the stomach 14 wall and allow the wall of tissue to slide along the length of the outer sleeve 318 proximally to the second catheter 328.

Figure 9:
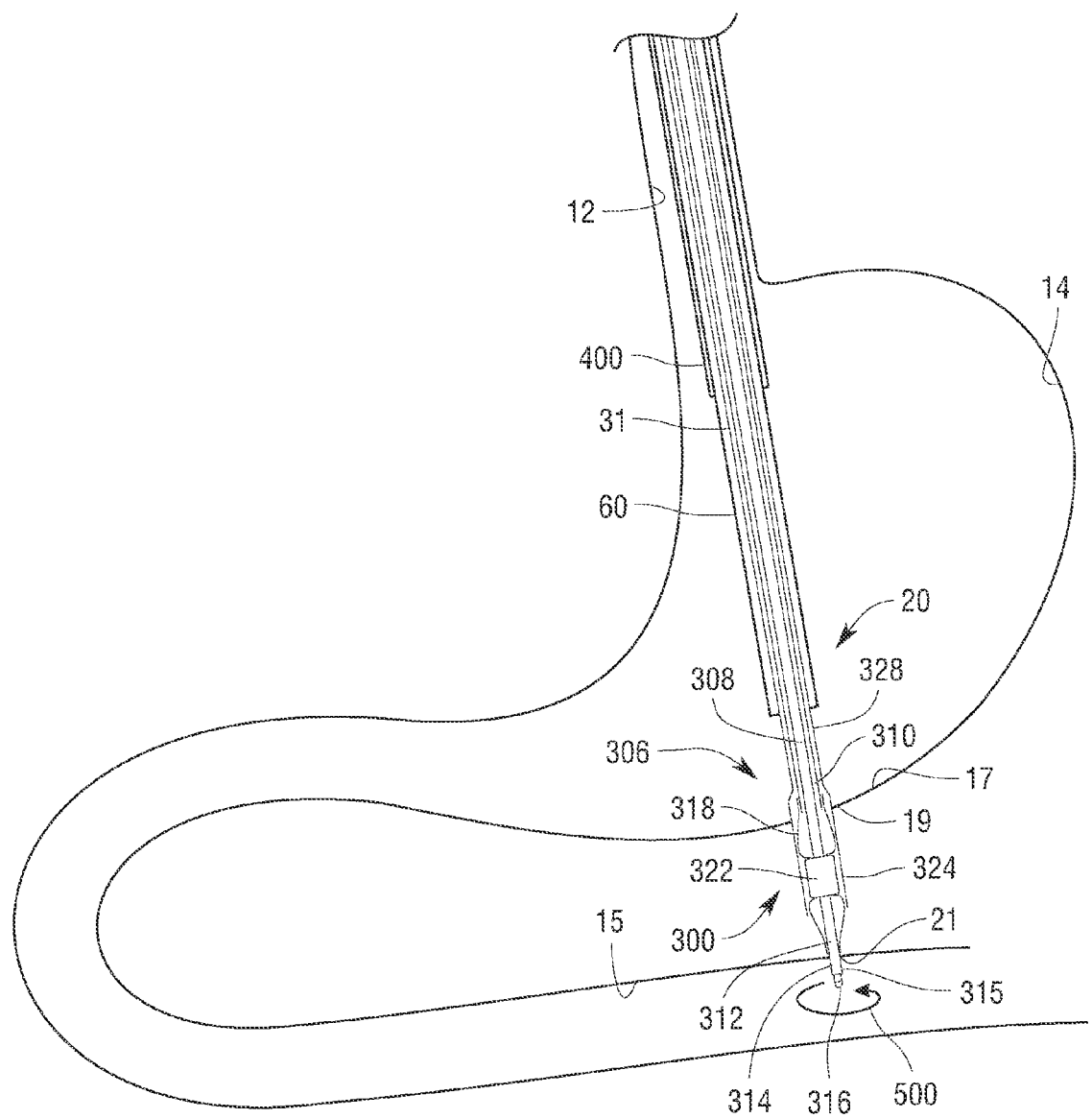
FIG. 9 is another diagrammatical view of a portion of the patient's gastrointestinal tract depicted in FIG. 7 wherein the surgical instrument of FIG. 3 has been inserted through the stomach to puncture through a portion of the jejunum.

FIG. 9 is another diagrammatical view of the patient's esophagus 12, stomach 14, and jejunum 15 depicted in FIG. 7, wherein the surgical instrument 20 has been inserted through the stomach 14 to puncture through a portion of the jejunum 15. Once the magnet placement device 320 has been located through the opening 19, the hole-forming instrument 312 may be used to form a second opening 21 in another lumen, in this example, the jejunum 15. The second opening 21 may be formed in a manner substantially similar to the first opening 19.

Figure 10:
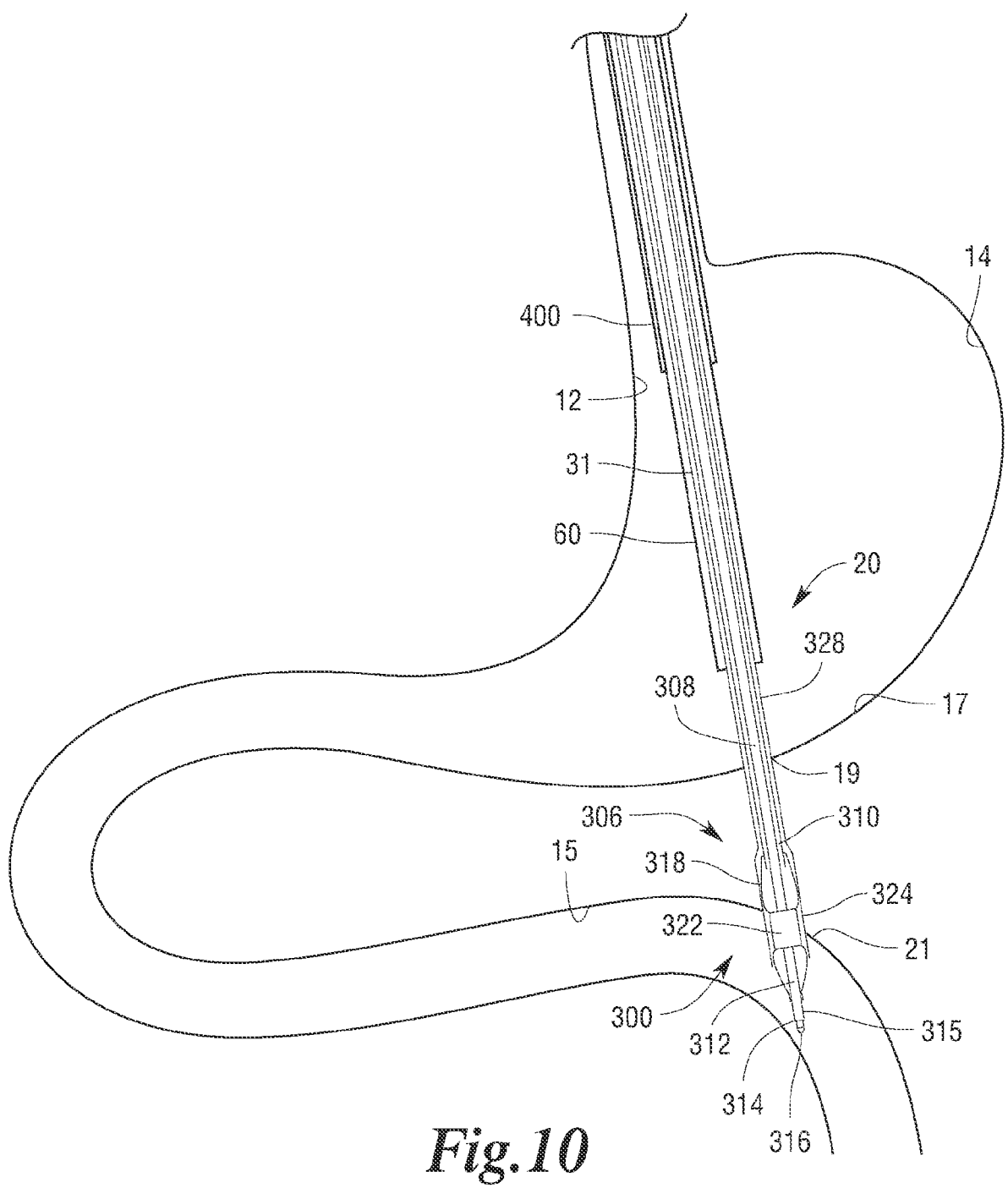
FIG. 10 is another diagrammatical view of a portion of the patient's gastrointestinal tract depicted in FIG. 7, wherein the hole-forming instrument has punctured a portion of the jejunum and at least a portion of the magnet placement assembly has been located within the jejunum.

FIG. 10 is another diagrammatical view of the patient's esophagus 12, stomach 14, and jejunum 15 depicted in FIG. 7, wherein the hole-forming instrument 312 has punctured a portion of the jejunum 15 and at least a portion of the magnet placement assembly 320 has been located within the jejunum 15. The magnet placement assembly 320 may be located within the jejunum 15 through the second opening 21 using a method substantially similar to the method used to locate the magnet placement assembly 320 through the first opening 19.

Figure 11A:
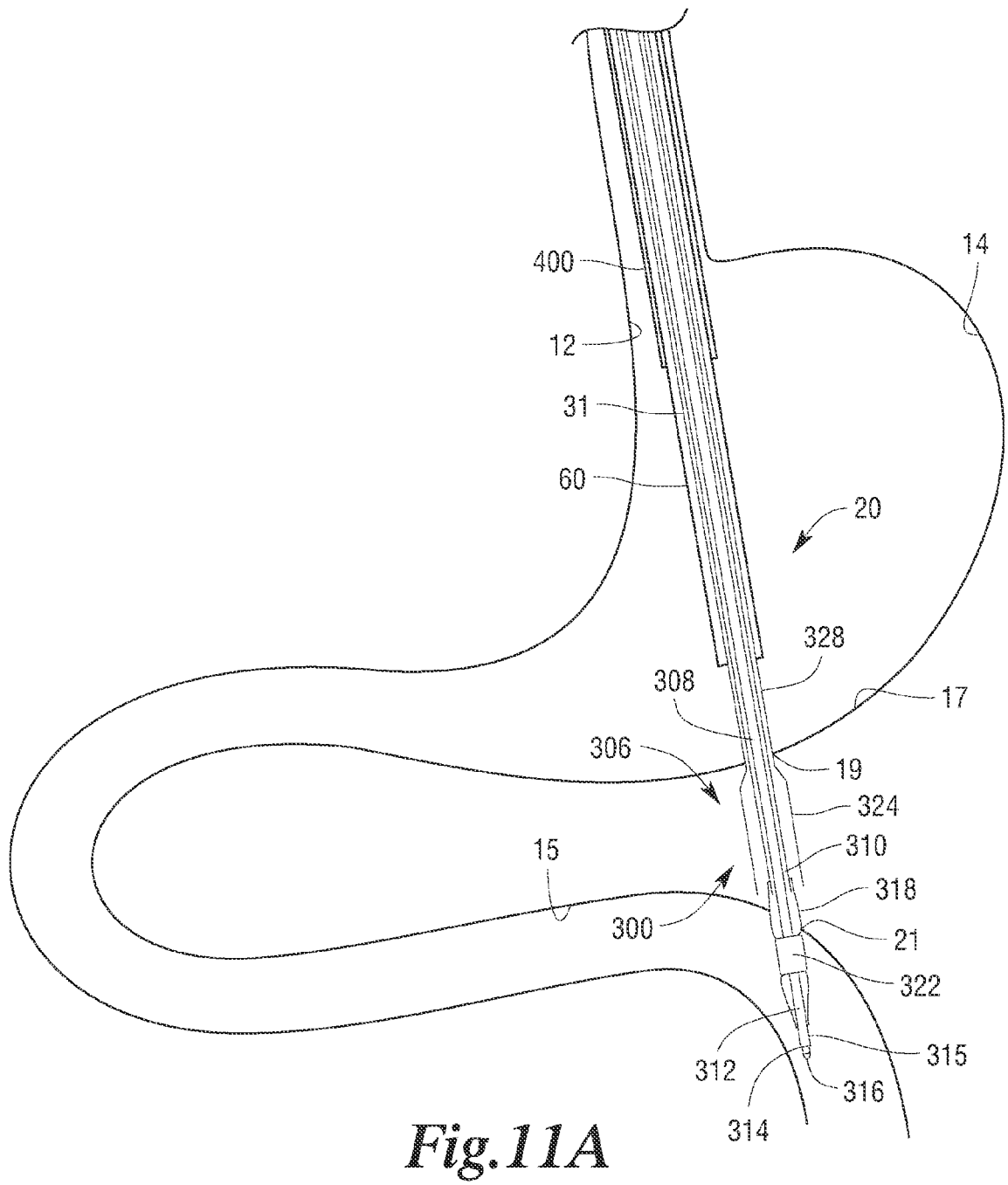
FIG. 11A is another diagrammatical view of a portion of the patient's gastrointestinal tract depicted in FIG. 7, wherein the magnet placement assembly is located within the jejunum and an outer sleeve has been retracted.
Figure 11B:
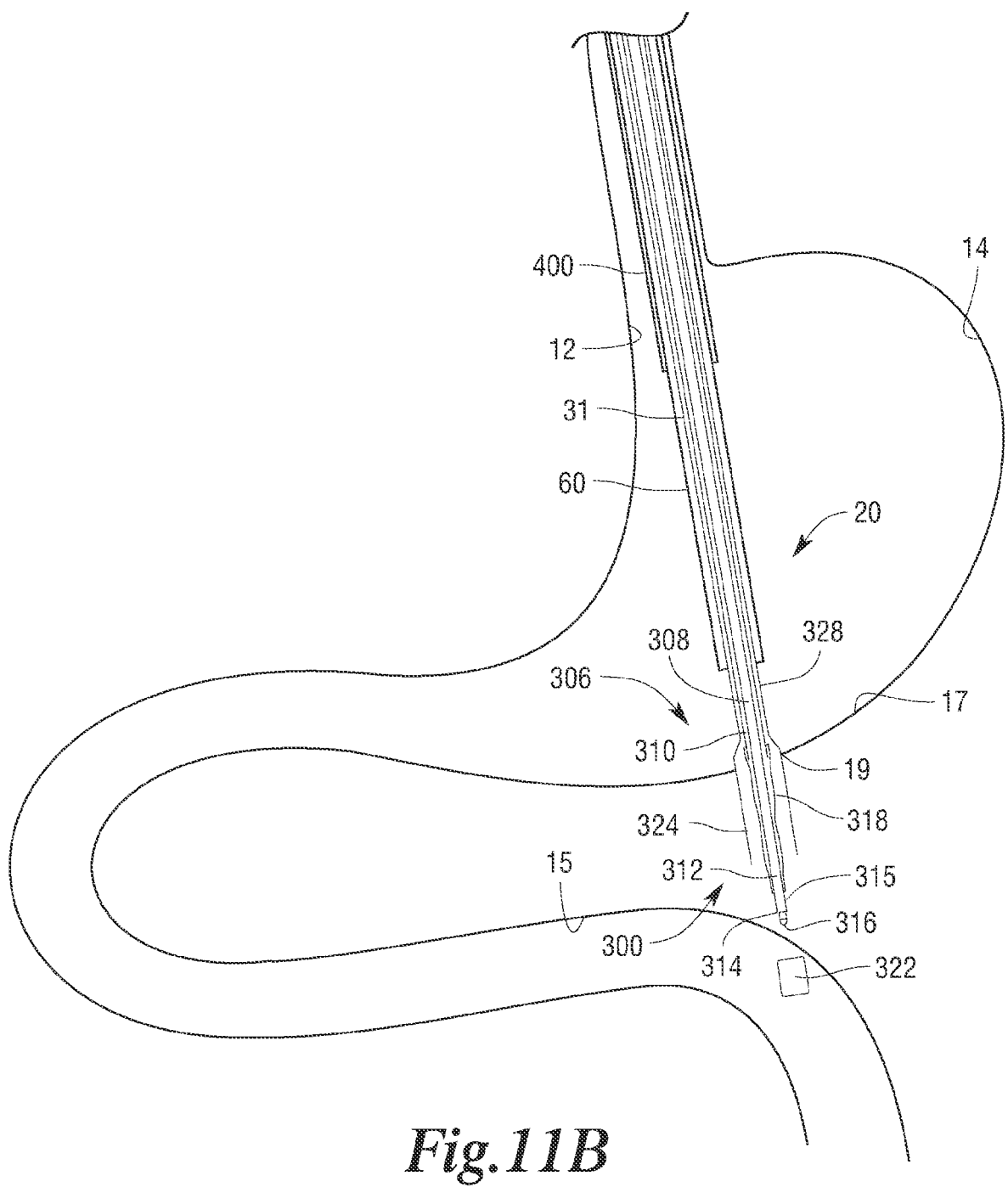
FIG. 11B is another diagrammatical view of a portion of the patient's gastrointestinal tract depicted in FIG. 7, wherein a magnet has been located within the jejunum and the surgical instrument has been removed from the jejunum.

FIG. 11A is another diagrammatical view of the patient's esophagus 12, stomach 14, and jejunum 15 depicted in FIG. 7, wherein the magnet placement assembly 320 is located at least partially within the jejunum 15 and the outer sleeve 324 has been retracted. As depicted in FIG. 11A, once a portion of the magnet placement assembly 320, including at least the magnet 322, is located within the jejunum 15, the outer sleeve 324 may be at least partially retracted proximally to expose the magnet 322. FIG. 11B is another diagrammatical view of the patient's esophagus 12, stomach 14, and jejunum 15 depicted in FIG. 7, wherein the magnet 322 has been located within the jejunum 15 and the surgical instrument 20 has been removed from the jejunum 20. As shown in FIG. 11B, once the magnet 322 has been exposed, the inflatable member 318 may be at least partially deflated to allow the magnet 322 to be placed within the jejunum 15. The magnet placement assembly 320 may be placed within the jejunum 15 by moving, shaking, jerking, and/or otherwise moving the magnet placement assembly 320 in a suitable manner to enable the magnet 322 to be located within the jejunum.

In one embodiment, upon placement of the magnet 322 within the jejunum 15, the surgical instrument 20, including the magnet placement assembly 320, without the magnet 322, may be retracted proximally. The surgical instrument 20 may be retracted from the second opening 21 and the first opening 19. The surgical instrument 20 may be completely retracted proximally from the patient's body through the mouth 10 (FIG. 1). Once the surgical instrument 20 has been sufficiently retracted, a second magnet 323 may be placed on the magnet placement assembly 320. The second magnet 323 may be substantially similar to the first magnet 322. In one embodiment, the second magnet 323 may be substantially identical to the first magnet 322. The second magnet 323 may be placed on the magnet placement assembly 320 in a manner substantially similar, if not identical, to the manner of placing the first magnet 322 on the magnet placement assembly 320.

Figure 12:
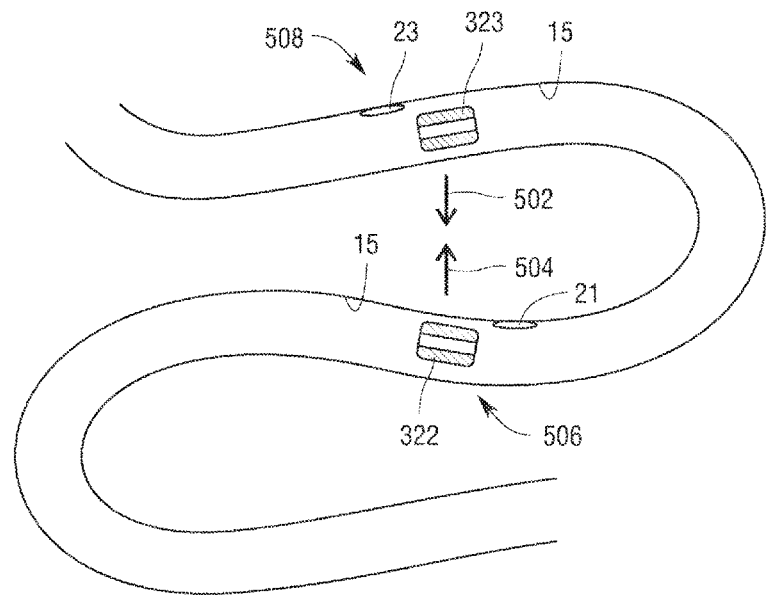
FIG. 12 is another diagrammatical view of a portion of the patient's gastrointestinal tract, wherein a first magnet is located in a first portion of the jejunum and a second magnet is located within a second portion of the jejunum.

In one embodiment, the surgical instrument 20 may be placed back into the patient's body through the mouth 10. FIG. 12 is another diagrammatical view of two portions of the patient's jejunum 15, wherein the first magnet 322 is located in the first portion of the jejunum 15 and the second magnet 323 is located within the second portion of the jejunum. The surgical instrument 20 may be located within the stomach 14 for a gastro-jejunum anastomosis, or may be located through the first opening 19 to create a third opening 23. To create a jejunum-jejunum anastomosis, the third opening 23 may be formed using the hole-forming instrument 312 of the surgical instrument 20. The third opening 23 may be formed in a manner substantially similar to the manner of creating the first opening 19 and the second opening 21. Once the third opening 23 has been formed in the jejunum 15, at least a portion of the magnet placement assembly 320 may be located within the jejunum 15 through the third opening 23. Once at least a portion of the magnet placement assembly 320 has been located within the third opening 23, the outer sleeve 324 may be retracted, and the second magnet 323 may be placed within the third opening 23 of the jejunum 15 in a manner substantially similar to the manner of placing the first magnet 322 within the second opening 21. Once the second magnet 323 has been placed, the surgical instrument 20 may be retracted proximally from the third opening 23, the first opening 19, and proximally from the patient's mouth 10.

In one embodiment, the first opening 19, the second opening 21, and/or the third opening 23 may be closed using another surgical instrument (not shown). One such instrument is referred to as a tissue apposition system (TAS), which may be employed to attach a tissue anchor such as a T-tag. The alternative surgical instrument may comprise an endoscopic stapler and/or any other suitable closure device. The endoscopic stapler may be used to staple the first opening 19, the second opening 21, and/or the third opening 23, thus effectively closing these openings 19, 21, 23.

Figure 13:
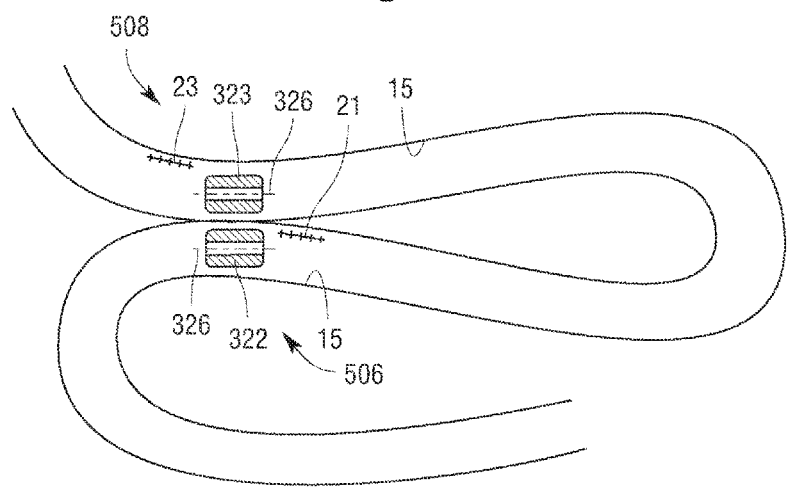
FIG. 13 is another diagrammatical view of a portion of the patient's gastrointestinal tract depicted in FIG. 12, wherein the first and second magnets are magnetically attracted to each other.

The first magnet 322 and the second magnet 323 may be attracted due to their respective magnetic polarizations. The first magnet 322 may be attracted to the second magnet 323 in the direction indicated by arrow 504, and the second magnet 323 may be attracted to the first magnet 322 in the direction indicated by arrow 502. FIG. 13 is another diagrammatical view of two portions of the patient's jejunum 15, wherein the first magnet 322 and the second magnet 323 have been magnetically attracted to each other. The first magnet 322 and the second magnet 323 may attract each other in a direction perpendicular to the axes 326 of the magnets 322, 323. Magnetic force may be applied by the first magnet 322 and the second magnet 323 to draw the first portion 506 of the jejunum 15 toward the second portion 508 of the jejunum 15 such that the first magnet 322 retains the first portion 506 of the jejunum 15 in sealing contact with the second magnet 323 and second portion 508 of the jejunum 15 to create an anastomosis between the first portion 506 and the second portion 508 of the jejunum 15.

Figure 14:
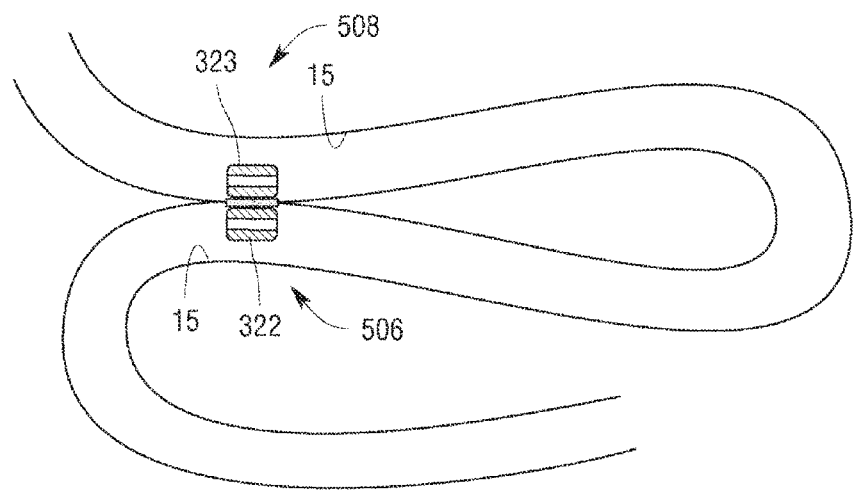
FIG. 14 is another diagrammatical view of a portion of the patient's gastrointestinal tract depicted in FIG. 12, wherein the first and second magnets have been attracted to each other and have begun to form an anastomosis between the first portion of the jejunum stomach and the portion of the jejunum.

FIG. 14 is another diagrammatical view of two portions of the patient's jejunum 15, wherein the first and second magnets 322, 323 have been attracted to each other and have begun to form an anastomosis between a first portion of the jejunum 15 and a second portion of the jejunum 15.

Figure 15:
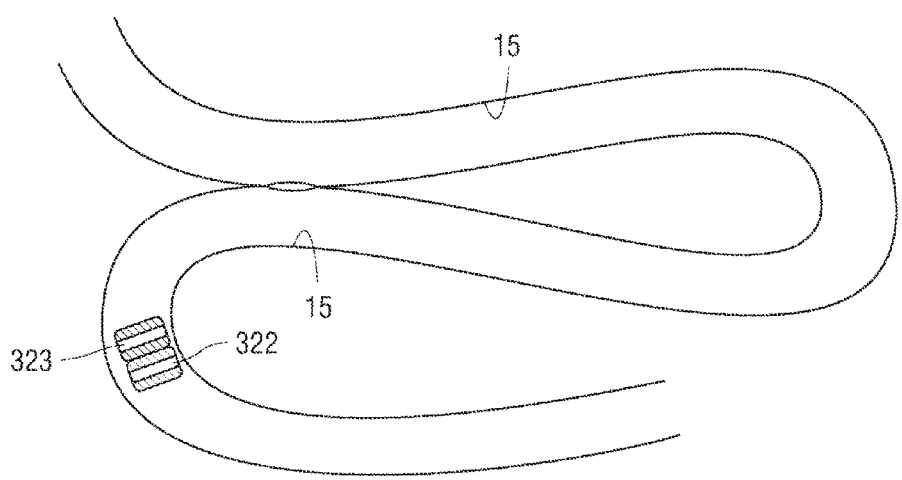
FIG. 15 is another diagrammatical view of a portion of the patient's gastrointestinal tract depicted in FIG. 12, wherein the first and second magnets have formed an anastomosis and have begun to pass through the gastrointestinal tract.

FIG. 15 is another diagrammatical view of a portion of the patient's gastrointestinal tract, wherein the first and second magnets 322, 323 have formed an anastomosis 350 and have begun to pass through the gastrointestinal tract. After a period of time, such as, seven to ten days, for example, the first magnet 322 and the second magnet 323 can pass naturally out through the small intestine leaving a permanent anastomosis 350.

The device which is intended to be protected is not to be construed as limited to the particular embodiments disclosed. The embodiments are therefore to be regarded as illustrative rather than restrictive. Variations and changes may be made by others without departing from the scope of the present invention. Accordingly, it is expressly intended that all such equivalents, variations and changes which fall within the scope of the present invention as defined in the claims be embraced thereby.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Although various embodiments have been described herein, many modifications and variations to those embodiments may be implemented. For example, different types of endoscopic needle assemblies may be employed. In addition, combinations of the described embodiments may be used. Also, where materials are disclosed for certain components, other materials may be used. The foregoing description and following claims are intended to cover all such modification and variations. It should be apparent, however, that various modifications, alterations and adaptations to those embodiments may occur to persons skilled in the art. For example, a single component may be replaced by multiple components, and multiple components may be replaced by a single component, to perform a given function or functions. This disclosure is therefore intended to cover all such modifications, alterations and adaptations without departing from the scope of the appended claims.

While the present disclosure illustrates and describes several embodiments in considerable detail, it is not the intention of the applicant to restrict or in any way limit the scope of the appended claims to such detail. Additional advantages and modifications may readily appear to those skilled in the art. Those of ordinary skill in the art will readily appreciate the different advantages provided by these various embodiments. While the various surgical instruments have been herein described in connection with the formation of a gastro-jejunostomy through a patient's mouth, those of ordinary skill in the art will readily appreciate that the unique and novel features of the various embodiments may be effectively employed in connection with forming an anastomosis between other organs which may be accessed through other natural orifices in the patient. In addition, it is conceivable that the various embodiments could have utility in some laparoscopic surgical procedures and therapies.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument for forming an anastomosis between two lumens, the surgical instrument comprising:
a first catheter comprising a proximal end, a distal end, at least one first opening and at least one second opening, the at least one first opening configured to slidably receive a hollow needle from the proximal end to the distal end of the first catheter;

a hollow sleeve slidably receivable over the distal end of the first catheter;

a magnet defining an opening there-through, wherein the magnet is retained within the hollow sleeve;

an inflatable member mounted near the distal end of the first catheter and in fluid communication with the at least one second opening, wherein the inflatable member is configured to pass through the opening of the magnet when the inflatable member is in a deflated state, retain the magnet when the inflatable member is in an inflated state, wherein the hollow sleeve retains at least a portion of the inflatable member in an inflated state, wherein the hollow sleeve is slidably removable from the magnet and the inflatable member, and be removed from the magnet when the inflatable member is in a deflated state; and wherein the inflatable member is inflatable to an inner diameter of the hollow sleeve, wherein the hollow sleeve prevents over inflation of the inflatable member, and wherein the inflatable member may be deflated when the hollow sleeve is slidably removed from the magnet and inflatable member.

2. The surgical instrument of claim 1, wherein the hollow needle comprises a rotary needle.

3. The surgical instrument of claim 2, wherein the rotary needle is rotatable by rotating a proximal portion of the rotary needle to penetrate tissue at a distal end of the rotary needle.

4. The surgical instrument of claim 2, wherein the rotary needle is chamfered around a periphery of the rotary needle at a distal end of the rotary needle.

5. The surgical instrument of claim 1 comprising a guide wire configured to be slidably disposed within the hollow needle, wherein the guide wire extends from the proximal end to the distal end of the first catheter.

6. The surgical instrument of claim 1, wherein the magnet comprises a cylindrical body, and wherein the opening is defined along an axis of the cylindrical body.

7. The surgical instrument of claim 6, wherein the magnet is diametrically polarized.

8. The surgical instrument of claim 1, wherein the hollow sleeve is configured to retain a guide wire, the hollow needle, and the magnet.

9. The surgical instrument of claim 1, wherein the hollow sleeve is attached to a second catheter, the second catheter configured to slidably retain the first catheter and extending from the distal end of the first catheter to near the proximal end of the first catheter.

10. The surgical instrument of claim 1 comprising a Y portion connected to the proximal end of the first catheter, wherein the Y portion comprises a first portion connected to the proximal end of the first catheter, a second portion, and a third portion.

11. The surgical instrument of claim 10, wherein the second portion of the Y portion is in communication with the first opening, wherein the hollow needle and the guide wire extend from the second portion of the Y portion at a proximal end of the surgical instrument, and wherein the third portion of the Y portion is in fluid communication with the second opening.

12. A method for forming an anastomosis between first and second lumens in a patient, comprising:

placing a first magnet within a hollow outer sleeve slidably receivable over a catheter, the first magnet having a cylindrical body defining an opening along an axis of the cylindrical body, wherein the first magnet is diametrically polarized;

forming a first opening in the first lumen, wherein the first opening is formed by a tissue penetrating tip attached to the catheter;

inserting the catheter, the tissue penetrating tip, and the hollow outer sleeve through the first opening;

forming a second opening in the second lumen using the tissue penetrating tip;

inserting the catheter, the tissue penetrating tip, and the hollow outer sleeve within the second opening;

inserting an inflatable member through the opening of the first magnet;

inflating the inflatable member within the hollow outer sleeve to form a contiguous surface from a proximal portion of the hollow outer sleeve to a distal portion of the hollow outer sleeve such that the first magnet is retained on the inflatable member;

retracting the hollow outer sleeve in a distal direction to expose the inflatable member and the first magnet;

deflating the inflatable member to allow the inflatable member to be withdrawn from the opening of the first magnet to place the first magnet within the second opening;

removing the hollow outer sleeve and inflatable member from the first and second openings;

placing a second magnet within the hollow outer sleeve, wherein the second magnet is substantially similar to the first magnet;

inserting the hollow outer sleeve through the first opening;

inserting the inflatable member through the opening of the second magnet;

inflating the inflatable member within the hollow outer sleeve to form a contiguous surface from a proximal portion of the hollow outer sleeve to a distal portion of the hollow outer sleeve such that the second magnet is retained on the inflatable member;

retracting the hollow outer sleeve in a distal direction to expose the inflatable member and the second magnet;

deflating the inflatable member to allow the inflatable member to be withdrawn from the opening of the second magnet to place the second magnet within the first opening;

attracting the first magnet toward the second magnet using magnetic force wherein the first magnet retains the second magnet in contact with the first lumen to create an anastomosis between the first and second lumens.

13. The method of claim 12 comprising passing a hole-forming instrument through a natural orifice in the patient into the first lumen, creating the first opening in the first lumen by placing a rotary needle in contact with the first lumen and rotating the rotary needle to form the first opening in the first lumen.

14. The method of claim 12 comprising inserting a guide wire, a balloon, and a hole-forming instrument of a magnet placement assembly through the opening of the first magnet.

15. The method of claim 12, comprising:

inflating a balloon to form a contiguous surface from a distal portion of a magnet placement assembly to a distal portion of a sleeve partially surrounding the magnet placement assembly;

locating the magnet placement assembly and the sleeve through the first opening and the second opening;

retracting the sleeve proximally to fully expose the first magnet;

deflating the balloon; and moving the magnet placement assembly to allow the first magnet to drop from the magnet placement assembly into the second lumen.

* * * * *

UNITED STATES PATENT AND TRADEMARK OFFICE
CERTIFICATE OF CORRECTION

| | | |
|---|---|---|
| PATENT NO. | : 8,828,031 B2 | Page 1 of 1 |
| APPLICATION NO. | : 12/352451 | |
| DATED | : September 9, 2014 | |
| INVENTOR(S) | : Fox et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1048 days.

Signed and Sealed this
First Day of March, 2016

Michelle K. Lee
*Director of the United States Patent and Trademark Office*